US006880615B2

(12) United States Patent
Cser

(10) Patent No.: US 6,880,615 B2
(45) Date of Patent: Apr. 19, 2005

(54) CENTRIFUGAL CASTING METHOD, CENTRIFUGAL CASTING DEVICE, HOLLOW CASTING MOLD AND FEED TROUGH FORMING DEVICE

(76) Inventor: Sandor Cser, Am Oberen Bühl 13, D-97350 Mainbernheim (DE)

( * ) Notice: Subject to any disclaimer, the term of this patent is extended or adjusted under 35 U.S.C. 154(b) by 0 days.

(21) Appl. No.: 10/333,001

(22) PCT Filed: Jul. 5, 2001

(86) PCT No.: PCT/DE01/02421

§ 371 (c)(1),
(2), (4) Date: Jul. 22, 2003

(87) PCT Pub. No.: WO02/05988

PCT Pub. Date: Jan. 24, 2002

(65) Prior Publication Data

US 2004/0026063 A1 Feb. 12, 2004

(30) Foreign Application Priority Data

Jul. 15, 2000 (DE) .......................... 100 34 641

(51) Int. Cl.[7] .............................................. B22D 13/00
(52) U.S. Cl. ...................... 164/114; 164/290; 164/298
(58) Field of Search ................................ 164/114, 290, 164/298, 35

(56) References Cited

U.S. PATENT DOCUMENTS

| | | | | |
|---|---|---|---|---|
| 1,876,261 A | * | 9/1932 | Pemetzrieder | 164/290 |
| 3,799,240 A | * | 3/1974 | Baumann et al. | 164/298 |
| 4,203,483 A | * | 5/1980 | Baumann et al. | 164/116 |
| 4,874,565 A | * | 10/1989 | Preston | 264/37.18 |
| 4,972,897 A | * | 11/1990 | Thomas | 164/35 |
| 5,091,148 A | * | 2/1992 | Prasad | 420/417 |
| 5,609,483 A | * | 3/1997 | Thomsen | 433/202.1 |
| 5,626,179 A | * | 5/1997 | Choudhury et al. | 164/66.1 |
| 5,980,792 A | | 11/1999 | Chamlee | |
| 6,386,265 B1 | * | 5/2002 | Usui | 164/114 |
| 6,572,815 B1 | * | 6/2003 | Ju et al. | 420/421 |
| 6,589,470 B1 | * | 7/2003 | Fried et al. | 264/443 |

FOREIGN PATENT DOCUMENTS

| | | |
|---|---|---|
| DE | 77 768 | 12/1893 |
| DE | 715 260 | 11/1941 |
| DE | 715260 | * 12/1941 |
| DE | 2 104 147 | 4/1972 |
| DE | 35 46 188 C2 | 7/1987 |
| DE | 195 05 689 A1 | 8/1996 |
| FR | 852514 | 10/1938 |
| FR | 1346299 | 10/1962 |
| GB | 362035 | 12/1931 |
| JP | 08 057 619 | 3/1996 |
| WO | WO 93/08942 | 5/1993 |

OTHER PUBLICATIONS

Serie von Hans–H. Caesar, Murr, Sep. 1984, Vom Chrom–Kobalt–Molybdän–Guβ Zur Polierten Modellguβprothese, *Dental–Labor, XXXII*.

* cited by examiner

*Primary Examiner*—Kiley S. Stoner
*Assistant Examiner*—I.-H. Lin
(74) *Attorney, Agent, or Firm*—McGlew and Tuttle, P.C.

(57) ABSTRACT

A centrifugal casting method is provided for the manufacture of hollow molds and applications of this apparatus and method are provided. A centrifugal casting apparatus has a hollow mold (13) suitable for the centrifugal casting. For the manufacture of cast workpieces by the centrifugal casting method a plurality of mold cavities (14) formed by at least one hollow mold (13) are arranged and driven such that the mold cavities (14) rotate about a common axis of rotation (18). At least three mold cavities (14) which rotate in a single plane are provided.

11 Claims, 4 Drawing Sheets

CENTRIFUGAL CASTING METHOD, CENTRIFUGAL CASTING DEVICE, HOLLOW CASTING MOLD AND FEED TROUGH FORMING DEVICE

CROSS REFERENCE TO RELATED APPLICATION

This application is a 371 of PCT/DE01/02421 filed on Jul. 5, 2001.

FIELD OF THE INVENTION

The invention relates to a centrifugal casting method, a centrifugal casting apparatus and a hollow mold. The invention further relates to a runner bush molder for the manufacture of a hollow mold and the application of the method or apparatus according to the invention for the manufacture of specific workpieces from specific materials.

BACKGROUND OF THE INVENTION

In generic centrifugal casting methods the mold filling of the mold cavity in a hollow mold is based on the hollow mold being displaced around an axis of rotation in a rotational movement. As a result of this rotational movement, a corresponding centrifugal force acts on the liquid molten casting material during pouring in, pressing the casting material into the mold cavity and ensuring complete filling.

Depending on the density and heat capacity of the casting material, different rotation speeds are required for complete filling of the mold cavity. On the one hand, this is based on the fact that only a corresponding relatively weak centrifugal force acts on materials having a relatively low density, for example titanium, so that a correspondingly higher rotational speed must be selected to apply a sufficiently high filling force. In addition, materials having a low heat capacity such as titanium solidify relatively quickly so that complete filling of the mold cavity which requires sufficient flowability of the casting material must be accomplished in a very short time. A high rotational speed is again required for such short filling times.

In commercially available centrifugal casting apparatus for high-quality casting, such as those used for example in dental technology and jewelry manufacture, there is only one hollow mold which rotates at a certain distance about an axis of rotation located outside the hollow mold. From this it follows that considerable centrifugal forces act on the hollow mold itself. Thus, in order to keep the hollow mold on its rotational path in known centrifugal casting apparatus, solid mechanical superstructures are required to absorb the centrifugal forces and compensate for the imbalance produced by the rotating mass of the hollow mold and the mass of the casting material. The solid mechanical structure of known centrifugal casting apparatus results in a high weight with correspondingly high moments of inertia from which follow long acceleration or braking phases.

DE 195 05 689 A1 discloses a centrifugal casting apparatus with a reusable hollow mold in which mold cavities each of the same type are arranged in pairs such that they rotate about a common axis of rotation and can be filled through a common downgate. If more than two workpieces are to be cast at the same time using this known apparatus, the mold cavities each arranged in pairs are arranged one above the other in several layers so that they come to lie in several planes.

A disadvantage of this apparatus is that only an even number of workpieces of the same type can be produced in one centrifugal casting process. In addition, the overall height of the hollow mold varies as a function of the number of mold cavities provided together in the hollow mold so that, depending on the number of workpieces to be manufactured together in each casting process, different components are required for the superstructure of the centrifugal casting apparatus.

SUMMARY OF THE INVENTION

Starting from this prior art, it is an object of the present invention to propose a new centrifugal casting method, a new centrifugal casting apparatus, a new hollow mold suitable for centrifugal casting, a suitable runner bush molder for manufacturing such hollow molds and new types of applications of these apparatus and methods.

The invention is based on the fundamental idea that during the implementation of the centrifugal casting method, in order to increase the workpieces which can be manufactured in one casting process, three or more mold cavities rotate about one axis and are arranged such that they are intersected by a common plane. The arrangement of the various mold cavities according to the invention is thus to be understood as that formation in which the different mold cavities are arranged such that they extend at least partly in a common plane of rotation. Parts of the mold cavities in the sense of this invention are also the sprue runners which connect the cavity to delimit the actual casting workpiece to be manufactured with a runner bush into which the liquid casting material is poured. As a result, it is thus obviously not necessary for all mold cavities to be arranged exclusively in the common plane of intersection. Rather, the various mold cavities generally extend in sections over the common plane depending on shape and size in each case. Ultimately, in order to satisfy the principle according to the invention, it is for example sufficient if the discharge gates with which the sprue runners of the individual mold cavities open into the runner bush are intersected by the common plane of intersection.

As a result of the arrangement of the mold cavities in a common plane, a simple balancing of masses can be achieved between the mold cavities or the follow molds since imbalances caused by the mold cavities or hollow molds are substantially mutually compensated and thus the centrifugal forces to be absorbed by the centrifugal casting apparatus can be minimized.

Both re-usable hollow molds and dead hollow molds can be used to form the mold cavities when implementing the centrifugal casting method according to the invention.

In order to achieve as uniform as possible balancing of masses between the individual mold cavities, it is particularly advantageous if in an arrangement of n mold cavities, these are arranged offset as uniformly as possible by an angle of rotation of approximately 360°/n. That is, the various mold cavities lie on circular orbits offset with respect to one another with an intermediate angle of 360°/n so that only a small imbalance is obtained overall.

There are basically two design solutions for the development of the centrifugal casting apparatus for implementing the method according to the invention. According to a first embodiment of a centrifugal casting apparatus according to the invention, this is provided with at least three holding devices in each of which at least one hollow mold can be secured. Each of the hollow molds contains at least one mold cavity. According to the invention, the hollow molds are arranged in the holding device such that the mold cavities rotate in a single plane when the centrifugal casting apparatus is driven. If three hollow molds are used, for example, these can be arranged in a star shape, for example, on the centrifugal casting apparatus so that the imbalance caused by the mass of the individual hollow molds is compensated overall.

Since the weight of the individual hollow molds in such an embodiment can differ completely one from the other, for example, as a result of differently sized mold cavities in the individual hollow molds, it is especially advantageous if the various hollow molds are individually adjustable. For example, it is feasible that the distance between the individual hollow molds and the axis of rotation can be adjusted independently of one another so that the different moment of inertia of the various hollow molds can be compensated by changes in the rotational distance.

According to a second embodiment of a centrifugal casting apparatus according to the invention, this is provided with one holding device for attachment of a hollow mold. In this hollow mold however, there is not only one mold cavity but at least three mold cavities are incorporated. The holding device of the centrifugal casting apparatus must thus be designed such that the hollow mold is attachable in a fashion so that the mold cavities rotate about a common axis of rotation in a single plane when the centrifugal casting apparatus is driven. In other words, this means that in this centrifugal casting apparatus the hollow mold can rotate about an axis of rotation which, for example, extends through the center of gravity of the hollow mold. As a result of this arrangement, an extensive balancing of masses can be achieved overall during the rotational movement of the hollow mold since each mass point of the hollow mold substantially has a corresponding counterweight on the opposite side. Imbalances can then only be caused by the irregular shape and arrangement of the different mold cavities. However, the imbalance can be reduced to a tolerable level with a sufficiently uniform distribution of mold cavities which are as far as possible the same size. The individual mold cavities in the hollow mold are then preferably arranged substantially rotationally symmetrically about the principal axis of inertia of the hollow mold.

As already put forward, different casting materials require different centrifugal forces or casting times. According to a preferred embodiment, the rotational speed can be set at the centrifugal casting apparatus according to the invention depending on the hollow mold used and/or the material to be cast. By this means, for example, materials having a high heat capacity or high density, especially gold, can be cast at a relatively low rotational speed and materials having a low density and low heat capacity can be cast at relatively high rotational speeds.

In order to implement the centrifugal casting method according to the invention in a centrifugal casting apparatus according to the second embodiment, there is proposed a hollow mold in which at least three mold cavities are substantially arranged in a single plane.

In this case it is especially advantageous if on the hollow mold there is provided a runner bush into which open the discharge gates of the sprue runners provided on the individual molds. By this means it can be achieved that during pouring of the liquid casting material into the runner bush, the various mold cavities are filled substantially at the same time and thereby relatively uniformly.

The sprue runners can preferably extend from the discharge gates lying in the plane of intersection alternately obliquely upwards and radially downwards towards the outside. By this means the cavities which later form the actual cast workpiece can be packed more closely in the hollow mold since these cavities then come to lie in at least two planes lying one above the other and are connected to the discharge gates lying in the plane of intersection by the obliquely running sprue runners.

The runner bush itself should be constructed as rotationally symmetrically as possible in order to consequently have no influence itself on the resulting imbalance of the hollow mold.

In order to substantially eliminate any escape of liquid casting material poured into the runner bush, it is advantageous if the runner bush tapers upwards. Any escape of liquid casting material is reliably avoided by the overhanging upper edge of the runner bush thereby formed. This can be achieved constructively by the runner bush being constructed as conical at least in sections.

Circular ring-shaped muffle rings can be used to form hollow molds according to the invention. During the manufacture of the hollow mold, a model made of wax, for example, which has the positive shape of the desired mold cavities, is first manufactured. This model is arranged together with a runner bush molder at the center of the muffle ring and embedded in a molding material. After hardening the molding material, the model material is then expelled thermally, chemically or in an otherwise suitable fashion so that the hollow mold is formed as a result from the circular ring-shaped muffle ring and the mold material hardened therein. Alternatively to using a muffle ring, the hollow molds according to the invention can also be manufactured without a ring, for example, using suitably shaped casting apparatus.

If a circular ring-shaped muffle ring is used to manufacture the hollow mold according to the invention, the volume present in the muffle ring must be substantially completely filled to achieve the desired balancing of masses when the hollow mold is rotationally driven. If, however, only a relatively small embedding volume is required as a result of the small volume of the individual mold cavities or the small number of mold cavities overall, the wastage of an unnecessarily large embedding volume can be avoided by arranging insertion elements in the muffle ring. The available volume in the muffle ring is reduced by these insertion elements so that as a result, less embedding material is required to fill the remaining volume. When arranging the insertion elements in the muffle ring, care must naturally be paid to ensure that the insertion elements are placed such that a sufficient balancing of masses is again obtained overall and imbalances caused by the insertion elements are substantially avoided.

The centrifugal casting method according to the invention or the centrifugal casting apparatus or hollow mold suitable therefor can basically be used for any cast workpieces. However, their application for the manufacture of workpieces in high-quality casting, especially in the manufacture of pieces of jewelry, dentures or tool parts, offers particular advantages.

The centrifugal casting method according to the invention or the centrifugal casting apparatus or hollow mold suitable therefor can basically be used for any casting materials, for example, gold or steel. The application of the method according to the invention or the centrifugal casting apparatus or hollow mold suitable therefor offers to particular advantages for casting materials having low density, for example titanium, since these materials can only be east with unsatisfactory quality or with very expensive apparatus using conventional methods or apparatus because of the high rotational speeds required in this case.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
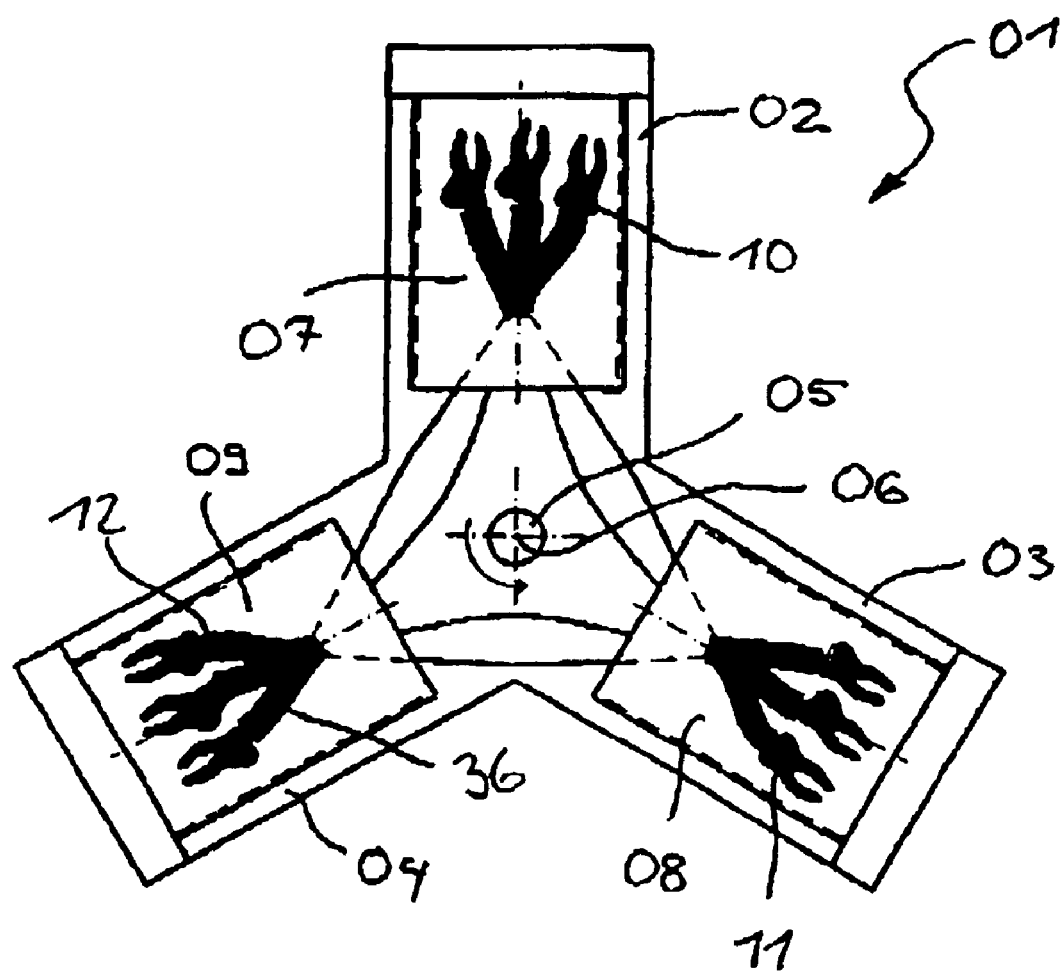
FIG. 1 is a schematic top view of a first embodiment of a centrifugal casting apparatus.

Referring to the drawings in particular, the centrifugal casting apparatus 01 shown in a schematic view in FIG. 1 has three holding devices 02, 03 and 04 arranged in a star shape which rotate jointly in a single plane about an axis of rotation 06 by driving a drive shaft 05.

A hollow mold 07, 08 or 09 can be attached to each holding device 02, 03 or 04. A mold cavity 10, 11 or 12 is incorporated in each of the hollow molds 07, 08 arid 09 by embedding and melting a suitably modeled wax model. Each mold cavity 10, 11 or 12 has three sprue runners which each connect a tooth-shaped cavity with a runner bush not shown In FIG. 1.

The radial distance of the individual hollow molds 07, 08 or 09 with respect to the axis of rotation 06 can be adjusted individually independently of one another in order to thereby compensate for mass imbalances.

During implementation of the centrifugal casting method according to the invention the three hollow molds 07, 08 and 09 rotate jointly in a single plane about the axis of rotation 06. When a sufficiently high rotational speed is reached, the liquid casting material is poured into the runner bush not shown in FIG. 1 and is pressed into the mold cavities 10, 11 or 12 as a result of the centrifugal forces thereby acting. As a result of the very highly adjustable rotational speeds according to the invention, substantially complete filling of the mold can be achieved in very short times so that materials with a low heat capacity or low density can be cast with sufficiently high quality.

Figure 2:
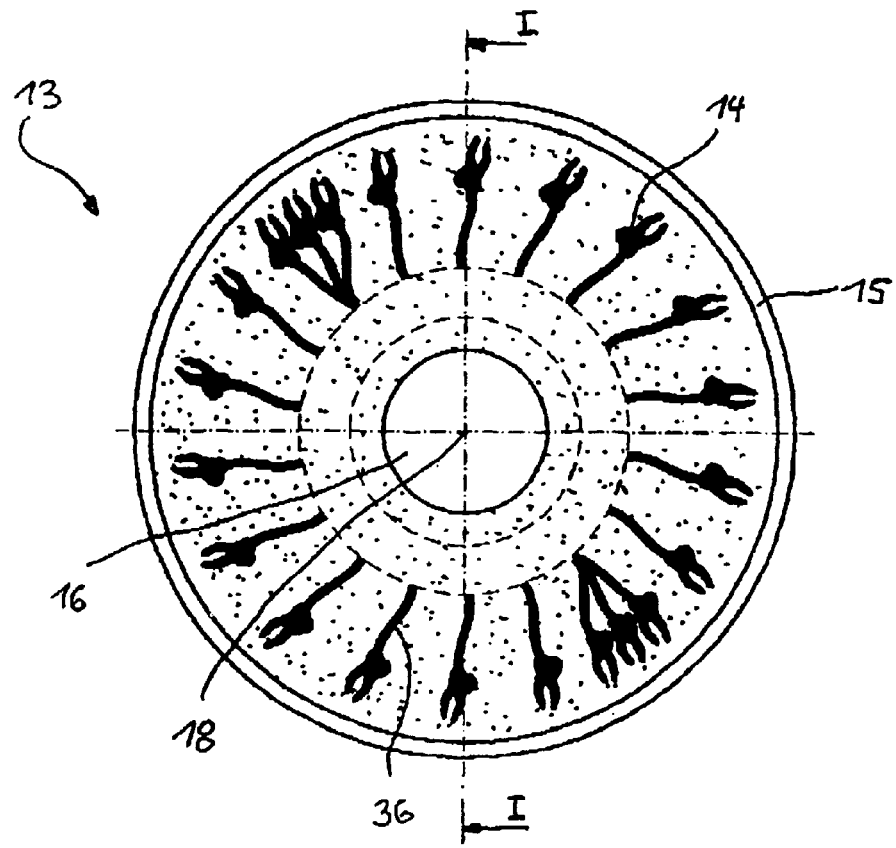
FIG. 2 is a schematic top view of a first embodiment oz a hollow mold.

FIG. 2 shows a top view of a hollow mold 13 wherein, to obtain a better understanding, the mold cavities 14 which are inherently unrecognizable from outside are shown with their respective adjoining sprue runners 36. The hollow mold 13 has a circular ring-shaped muffle ring 15, made of steel for example, at its external circumference. A model, made of wax for example, whose shape corresponds to the positive shape of the desired mold cavities 14 with sprue runners and a sectionally conical runner bush 16, is used in the manufacture of the hollow mold 13. To produce this model, the cast objects to be manufactured, e.g. dentures, are modeled in wax and then fused onto a standardized sprue runner molder using a standardized runner bush molder. The substantially rotationally symmetrically formed model thus produced is then arranged at the center of the muffle ring 15 and is subsequently embedded in a hardenable molding material 17. After the molding material 17 has hardened, the model material is removed by melting so that the desired negative shape of the mold cavities is formed in the molding material 17.

Figure 3:
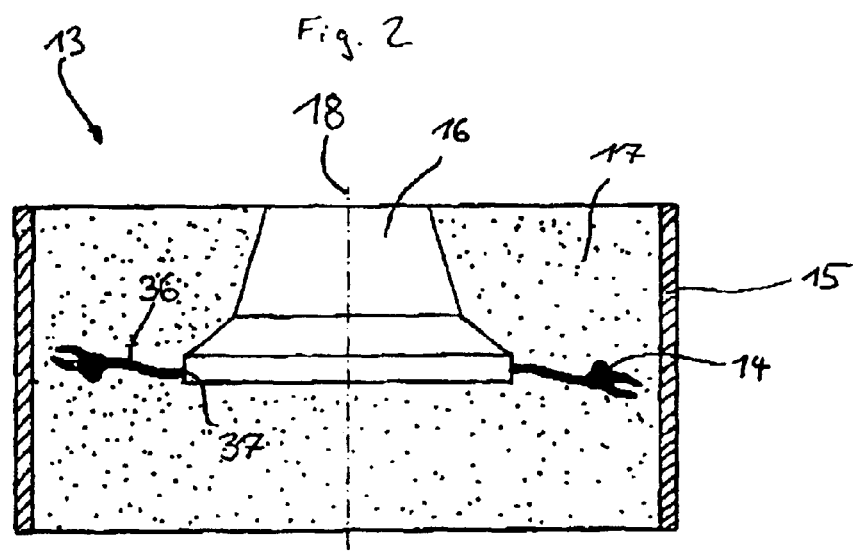
FIG. 3 is a cross-section along the line 1—1 of the hollow mold from FIG. 2.

As can be seen especially from FIG. 3, the individual mold cavities 14 and the runner bush 16 are arranged rotationally symmetrically with respect to the axis of rotation 18 of the hollow mold 13. In addition, all mold cavities 14 lie in a common plane around the principal axis of inertia 18. Each mold cavity has a sprue runner 36 with a discharge gate 37 so that the liquid casting material can flow from the runner bush 16 into the mold cavities 14. As a result, the hollow mold 13 can be arranged in a centrifugal casting apparatus so that the principal axis of inertia 18 runs along the axis of rotation of the centrifugal casting apparatus so that the imbalances occurring when the hollow mold is driven rotationally are substantially compensated and reduced to a permissible extent. During the actual casting process the liquid casting material is poured into the runner bush 16 while the hollow mold 13 rotates about the principal axis of inertia 18 at a sufficiently high rotational speed. As a result of the centrifugal forces acting on the casting material, the mold cavities 14 are cast quickly and substantially free of shrink holes.

Figure 4:
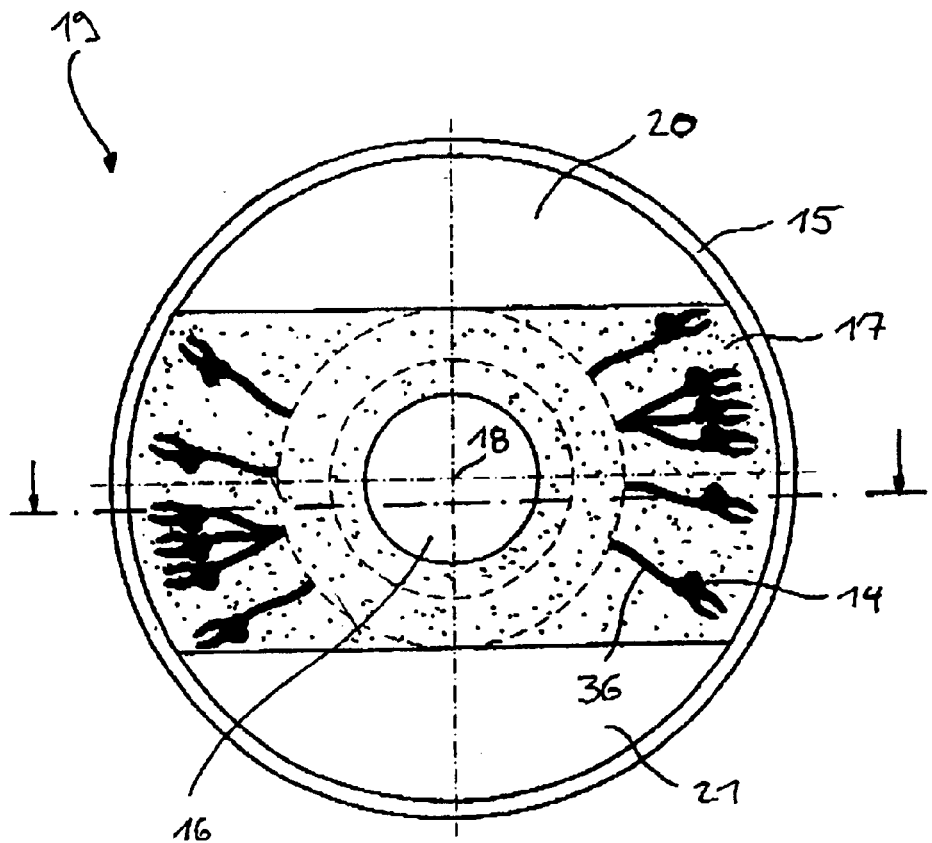
FIG. 4 is a schematic top view of a second embodiment of a hollow mold.
Figure 5:
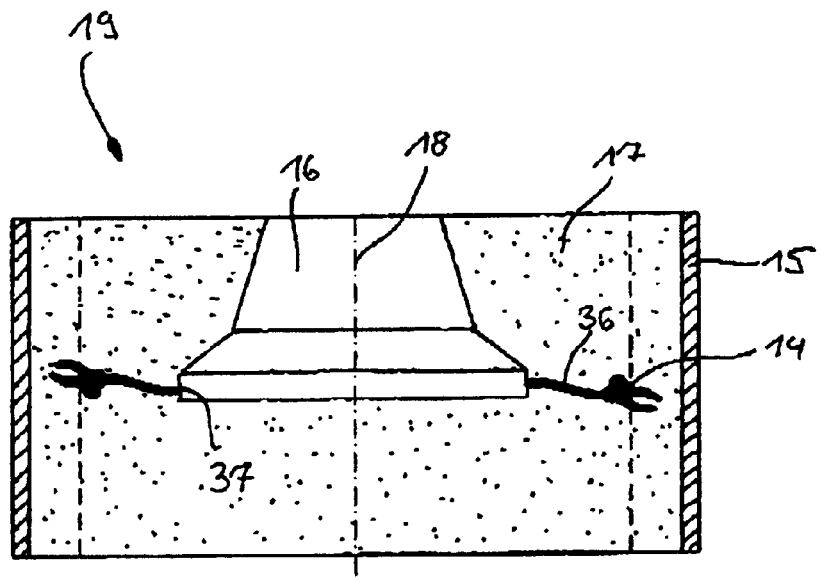
FIG. 5 is a cross-section along the line 11—11 of the hollow mold from FIG. 4.

The embodiment 19 of a hollow mold shown in FIG. 4 corresponds to the hollow mold 13 in terms of its essential structure. The circular ringshaped muffle ring 15 is again used and a runner bush 16 with adjoining sprue runners and mold cavities 14 is again provided in the hardenable molding material 17.

In order to make it possible to manufacture a relatively small number of workpieces, i.e., in the present case of dentures, in the hollow mold 19, two circular-segment-shaped insertion elements 20 or 21 can be arranged axially symmetrically with respect to one another in the muffle ring 15. By means of the insertion elements 20 and 21, the volume to be filled by the molding material 17 inside the muffle ring 15 is reduced wherein the inertia masses of the insertion elements 20 and 21 compensate for each other during a rotational movement of the hollow mold 19 around the principal axis of inertia 18.

The insertion elements 20 and 21 can be constructed as solid components or as hollow members, e.g., in the fashion of bent-sheet components, wherein a corresponding reduction in the inertial mass as a whole is obtained when bent-sheet components are used.

Figure 6:
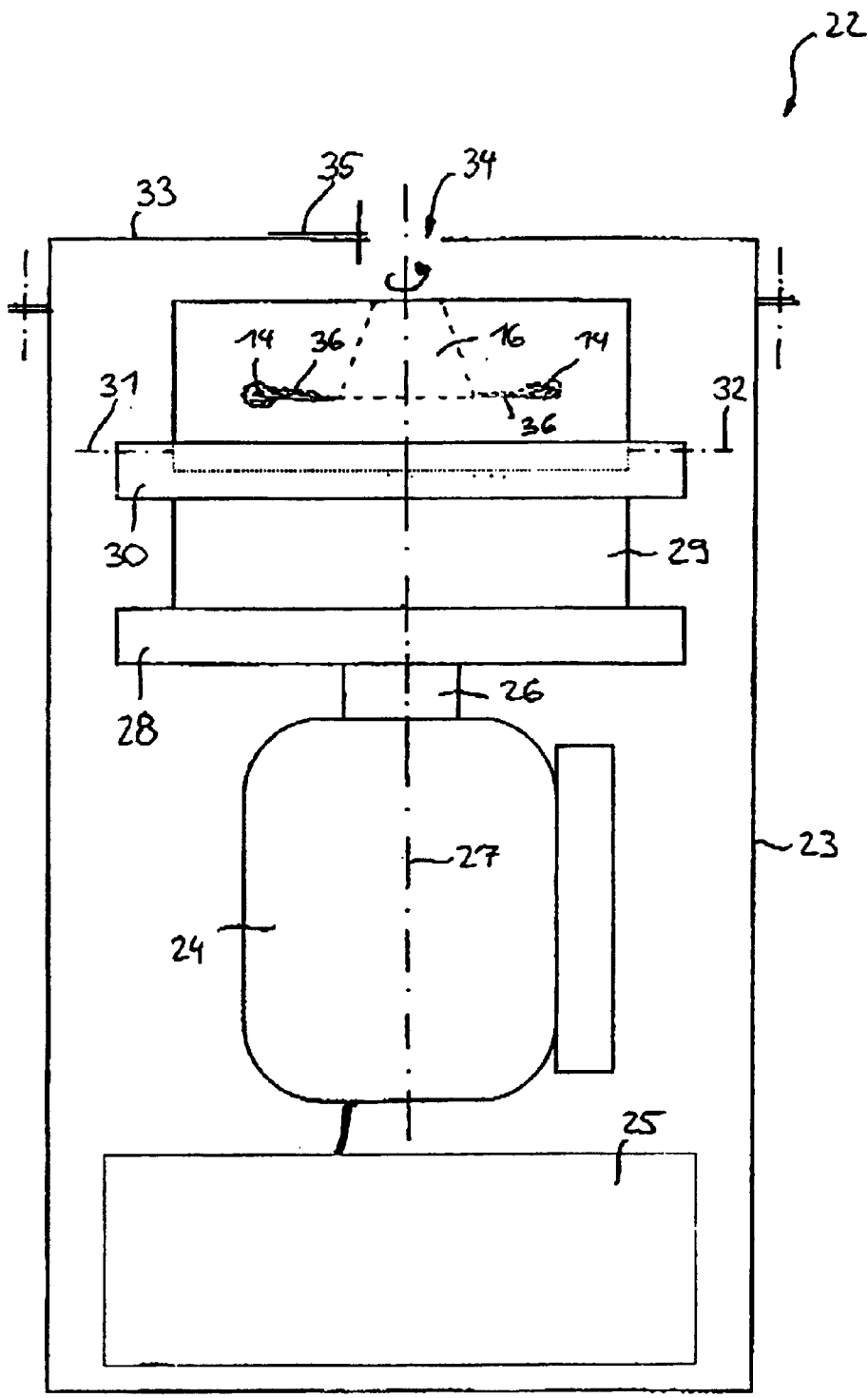
FIG. 6 is a centrifugal casting apparatus for use with hollow molds from FIG. 2 to FIG. 5.

FIG. 6 shows a schematic cross-section of a second embodiment 22 of a centrifugal casting apparatus. This is suitable for use with hollow molds 13 and 19 as shown in FIG. 2 to FIG. 5. The centrifugal casting apparatus 22 has a drive device 24, for example an electric motor, in a housing 23, which drive device is controlled or regulated using a control and regulating device 25 in accordance with settings preset by the operator. The drive shaft 26 can be driven rotationally by means of the drive unit 24 such that it rotates about a central axis 27. At the upper end of the drive axis 26 there is provided a base plate 28 on whose upper side a circular-disk-shaped holding device 30 can be attached with a spacer 29 arranged in between. The upper side of the holding device 30 has a circular-disk-shaped recess whose diameter is the same as the outside diameter of the hollow mold 13. The hollow mold 13 is attached to the holding device 30 by means of clamping devices 31 and 32, shown only schematically, which can be constructed in the fashion of clamping screws for example.

After attaching the hollow mold 13 to the base plate 30, a lid 33 is attached to the housing 23 from above so that the hollow mold 13 is enclosed towards the outside. Above the runner bush 16 the lid 33 has a recess 34 through which the molten casting material can be poured into the runner bush 16 from above. A rotatable lid 35 serves to cover the recess 34 after pouring in the liquid casting material.

As a result of the size and shape of the runner bush 16, special casting techniques such as bar casting or lost heads are no longer required as a reservoir to take care of solidification shrinkage. This function is fulfilled by the melt remaining in the runner bush since the casting material in this region is the last to solidify and can thereby be conveyed into the mold cavities 14.

While specific embodiments of the invention have been shown and described in detail to illustrate the application of the principles of the invention, it will be understood that the invention may be embodied otherwise without departing from such principles.

What is claimed is:

1. A centrifugal casting apparatus for implementing a method of rotating a plurality of mold cavities formed by at least one hollow mold, about a common axis of rotation and providing at least three mold cavities as the plurality of mold cavities which rotate about an axis and are intersected by at least one common plane, the apparatus comprising:

a dead hollow mold; and a holding device to attach the hollow mold containing at least three mold cavities, wherein the hollow mold can be arranged in the holding device so that the mold cavities rotate about an axis when the centrifugal casting apparatus driven and are intersected by a plane, wherein each of said mold cavities includes at least one runner with a discharge gate running from a rotationally symmetrical runner bush having a central axis extending substantially along the said axis of rotation, and each of said mold cavities is intersected by the common plane in the region of said sprue runners in the region of said discharge gate, and the liquid casting material can be poured into said runner bush so that said mold cavities can be filled with casting material by said sprue runners.

2. The centrifugal casting apparatus according to claim 1, wherein a number of n mold cavities used is arranged offset substantially uniformly by an angle of rotation of approximately 360°/n.

3. The centrifugal casting apparatus according to claim 1, wherein the hollow molds are individually adjustable.

4. The centrifugal casting apparatus according to claim 1, wherein the rotational speed can be adjusted depending on the hollow mold used and/or on the material to be cast.

5. The centrifugal casting apparatus according to claim 4, wherein the rotational speed is automatically adjustable.

6. The centrifugal casting apparatus according to claim 1, wherein said plurality of mold cavities cast form one or more of pieces of jewelry, dentures, semi-finished products for the manufacture of dentures or tool parts by centrifugal casting.

7. The centrifugal casting apparatus according to claim 1, wherein said runner bush tapers upwards from below and is constructed co ically at least in sections.

8. The centrifugal casting apparatus according to claim 1, wherein the external diameter of said hollow mold is formed by a circular ring-shaped muffle ring.

9. The centrifugal casting apparatus according claim 8, wherein insertion elements which abut positively on an inner circumference of said muffle ring can be arranged in said muffle ring in order to reduce the volume available for the production of said hollow mold in said muffle ring.

10. The centrifugal casting apparatus according to claim 1, wherein said runner bush molder is constructed circularly symmetrically and/or at least conically in sections.

11. The centrifugal casting apparatus according to claim 1, wherein said casting materials include a metal or an alloy with a low density including titanium.

* * * * *